US00PP30211P2

(12) United States Plant Patent
Bradford et al.

(10) Patent No.: US PP30,211 P2
(45) Date of Patent: Feb. 19, 2019

(54) NECTARINE TREE NAMED 'AUGUST TIME'

(50) Latin Name: *Prunus persica*
Varietal Denomination: August Time

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/732,741

(22) Filed: Dec. 26, 2017

(51) Int. Cl.
*A01H 5/08* (2018.01)

(52) U.S. Cl.
USPC ..... Plt./190

(58) Field of Classification Search
USPC ..... Plt./187, 190
See application file for complete search history.

(56) References Cited

U.S. PATENT DOCUMENTS

PP15,143 P2 9/2004 Bradford
PP16,462 P2 4/2006 Bradford

*Primary Examiner* — Susan McCormick Ewoldt

(57) ABSTRACT

The present invention relates to a new and distinct variety of nectarine tree, *Prunus persica*, broadly characterized by a medium to large size, vigorous, hardy, self-fertile, productive and regular bearing tree. The variety blooms during the mid to late season and requires about 600 chilling hours. The fruit matures under the ecological conditions described in mid August, with first picking on Aug. 12, 2017. The fruit is uniform, large in size, acidic with traditional nectarine flavor, globose to slightly elongated in shape, clingstone in type, firm and crisp in texture, yellow in flesh color, virtually full red in skin color, and has a bitter tasting kernel.

1 Drawing Sheet

Botanical classification: *Prunus persica.*
Variety denomination: 'AUGUST TIME'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'August Time'.

In 2003 we made a first generation hybridization using '34P572' (unpatented) nectarine as the selected seed parent and 'Candy Princess' (U.S. Plant Pat. No. 16,462) peach as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2008 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, '34P572' (unpatented) nectarine, by being self-fertile and by producing nectarines that are mostly red in skin color, that are yellow in flesh color, that are clingstone in type, and that are medium to large in size, but is quite distinguished from it by maturing about thirty-five days later.

The present variety is similar to its pollen parent, 'Candy Princess' (U.S. Plant Pat. No. 16,462) peach, by being self-fertile, by having a showy blossom, by blooming in the mid to late season, and by producing fruit that is mostly red in skin color and yellow in flesh color, but is quite distinguished from it by being a nectarine instead of peach, by having an acidic instead of sub-acidic flavor, and by maturing about thirty days later.

The present variety is most similar to 'August Bright' (U.S. Plant Pat. No. 15,143) nectarine by being self-fertile, by having a non-showy blossom, by blooming in the mid to late season, and by producing nectarines that mature in mid August and that are mostly red in skin color, yellow in flesh color, globose to slightly oblong in shape, clingstone in type, very good in flavor, but is distinguished therefrom by having a larger tree, by blooming more densely, by having globose instead of reniform leaf glands, and by producing fruit that is somewhat larger in size, that has much less skin freckling, that is sweeter in flavor, and that has a bitter instead of sweet kernel.

SUMMARY OF VARIETY

In summary, the present nectarine variety is characterized by a medium to large size, vigorous, hardy, self-fertile, productive and regular bearing tree. The variety blooms during the mid to late season and requires about 600 chilling hours. The fruit matures under the ecological conditions described in mid August, with first picking on Aug. 12, 2017. The fruit is uniform, large in size, acidic with traditional nectarine flavor, globose to slightly elongated in shape, clingstone in type, firm and crisp in texture, yellow in flesh color, virtually full red in skin color, and has a bitter tasting kernel.

DRAWING

The accompanying photograph consists of four whole fruits positioned to display the characteristics of the skin color and form, one sliced fruit to reveal the flesh and stone, typical leaves, a tip shoot of new leaf growth, and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 15, 2017, on a multiplied tree using Nemaguard (unpatented) root stock during its seventh growing season. The blossom and flower descriptions were made the previous blooming season. All major color code designations are by reference to the Inter-Society Color Council, National Bureau of Standards. Common color names are also used occasionally.

PARENTAGE

Seed parent: '34P572' (unpatented) nectarine.

Pollen parent: 'Candy Princess' (U.S. Plant Pat. No. 16,462) peach.

TREE

Size: Medium to large, reaching and maintaining a height of 12' [3.66 m.] and a spread of 9' [2.74 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 600 hours.

Leaf bud burst: Medium, during the middle of flowering.

Trunk:

*Size*.—Stocky, reaching a maximum diameter of 4½" [114.3 mm.] after the seventh growing season.

*Texture*.—Medium roughness.

*Bark color*.—A Grayish yellowish brown [80. gy.yBr] and Moderate yellowish brown [77. m.yBr] variegation with Strong yellowish brown [74. s.yBr] crevices present.

*Lenticels*.—Approximate Number Per Square Inch: 6. Color: Brownish orange [54. brO]. Average Size: ¼" [6.4 mm.] in length. The width is typically one fourth as much as the length. Shape: Eye-shaped and elongated.

Branches:

*Size*.—Stocky to medium, diameter of main scaffold is 2¾" [69.9 mm.] measured 12" above the crotch, diameter of limb is 1½" [38.1 mm.] measured 12" above the first fork.

*Texture*.—Smooth on first and second year wood, increasing in roughness with age.

*Color*.—1st Year Wood Topside: Grayish red [19. gy.R]. 1st Year Wood Underside: Brilliant yellow green [116. brill.YG]. 3rd Year Wood: A Light brown [57. l.Br] and Grayish brown [61. gy.Br] variegation with Moderate brown [58. m.Br] crevices present.

*Lenticels*.—Number Per Square Inch: About 30 on second year wood. Color: Deep brown [56. deep Br]. Average Size: Medium, 1/16" [1.6 mm.] in length. The width is typically one fourth as much as the length. Shape: Eye-shaped and elongated.

Leaves:

*Size*.—Large. Average Length: 6⅞" [175 mm.]. Average Width: 1⅝" [41.3 mm.].

*Arrangement*.—Alternate.

*Thickness*.—Medium.

*Form*.—Elliptical.

*Apex*.—Acuminate.

*Base*.—Acute to rounded.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: ½" [12.7 mm.]. Average Thickness: 1/16" [1.6 mm.]. Color: Moderate yellow green [120. m.YG].

*Stipules*.—Number: 2 per leaf, up to 6 per growing tip. Average Length: 5/16" [7.9 mm.]. Color: Vivid yellow green [115. v.YG] becoming Moderate brown [58. m.Br] with age.

*Glands*.—Number: 1 to 3 per leaf. Position: Alternate, first pair is located at the intersection of petiole and base of blade. Form: Globose. Size: Medium, about 1/32" [0.8 mm.] in diameter. Color: Brilliant yellow green [116. brill.YG] acquiring a Dark reddish brown [44. d.rBr] center with age.

*Leaf buds*.—Pointed.

Flower buds:

*Hardiness*.—Hardy, with respect to central California blooming season.

*Diameter*.—Typically 5/16" [7.9 mm.] 1 week before bloom.

*Length*.—Typically 9/16" [14.3 mm.] 1 week before bloom.

*Form*.—Not appressed.

*Surface*.—Slightly pubescent.

*Tip color*.—Moderate purplish pink [250. m.pPk].

Flowers: Perfect, complete, perigynous, usually a single pistil, about thirty stamens, five sepal and petal locations alternately positioned.

*Type*.—Non-showy, small.

*Average flower diameter*.—1" [25.4 mm.].

*Average flower depth*.—⅜" [9.5 mm.] when fully open.

*Average pedicel length*.—⅛" [3.2 mm.].

*Number of petals*.—Mostly five, double blossoms rarely observed.

*Petal arrangement*.—Overlapping.

*Petal shape*.—Rounded to oval.

*Petal margin*.—Entire, wavy with some notches present.

*Average petal diameter*.—5/16" [7.9 mm.].

*Average petal length*.—7/16" [11.1 mm.].

*Petal apex*.—Rounded.

*Petal base*.—Rounded to somewhat truncate.

*Petal color*.—Light purplish pink [249. l.pPk] toward the apex, Dark purplish pink [251. d.pPk] toward the base on both sides.

*Anther color*.—Very reddish orange [34. v.rO] at bloom onset.

*Pollen*.—Anthers produce an abundance of Brilliant yellow [83. brill.Y] pollen.

*Stigma color*.—Pale yellow green [121. p.YG].

*Stigma position*.—Located about ⅛" [3.2 mm.] above the nearby anthers.

*Stamen position*.—Typically located about 1/32" [0.8 mm.] below the petals.

*Ovary*.—Non-pubescent.

*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.

*Sepal length*.—5/16" [7.9 mm.].

*Sepal width*.—¼" [6.4 mm.].

*Sepal apex*.—Rounded to elliptical to match the sepal length and width.

*Sepal margin*.—Fairly smooth with occasional notches.

*Average pistil length*.—11/16" [17.5 mm.].

*Average stamen length*.—9/16" [14.3 mm.].

*Fragrance*.—Moderate.

*Blooming period*.—Mid to late compared to other varieties, two days before 'August Bright' (U.S. Plant Pat. No. 15,143) nectarine.

*Onset of bloom*.—One percent on Feb. 22, 2017.

*Date of full bloom*.—Mar. 2, 2017.

*Duration of bloom*.—One to two weeks, dependent on ambient temperature.

*Bloom density*.—Heavy.

*Number per cluster*.—1 to 3 with single flowers most common.

FRUIT

Maturity when described: Firm ripe, Aug. 15, 2017.

Date of first picking: Aug. 12, 2017.

Date of last picking: Aug. 22, 2017.

Size: Uniform, large.

*Average diameter axially*.—3¼" [82.6 mm.].

*Average diameter across suture plane*.—3⅛" [79.4 mm.].

*Average diameter across cheek plane*.—3 1/16" [77.8 mm.].

*Typical weight*.—10.4 ounces [295 grams].

Form: Mostly uniform, globose to slightly elongated, mostly symmetrical.

*Longitudinal section form*.—Round to slightly oval.

*Axial view*.—Round.

Suture: A shallow trough extending from the base, along the side, and ending about ½" [12.7 mm.] beyond the pistil point.

*Near the base*.—A shallow groove.

*Along the side*.—A shallow trough.

*Near the apex*.—A shallow groove.

Ventral surface: Rounded, lipped on both sides.

Lips: Fairly equal.

Cavity: Flaring, elongated in the suture plane, suture showing on one side, Brilliant yellow [83. brill.Y] stem markings present.

*Depth*.—½" [12.7 mm.].

*Breadth*.—1¼" [31.8 mm.].

Base: Truncate, slightly cordate if viewed parallel to the suture.

Apex: Rounded.

Pistil point: Negligible in length, some apical and some oblique, usually. depressed within the suture.

Stem: Medium.

*Average length*.—⅜" [9.5 mm.].

*Average width*.—3/16" [4.8 mm.].

Skin:

*Thickness*.—Medium.

*Surface*.—Smooth.

*Tenacity*.—Tenacious to the flesh.

*Astringency*.—Moderate.

*Tendency to crack*.—None observed.

*Color*.—Strong red [12. s.R] over a Moderate reddish orange [37. m.rO] background with moderate Very deep red [14. v.deep R] mottling throughout and virtually no freckling.

Flesh:

*Color*.—Brilliant orange yellow [67. brill.OY] with Dark red [16. d.R] flecking throughout.

*Surface of pit cavity*.—Covered with Dark red [16. d.R] broken fibers when twisted away from the stone.

*Amygdalin*.—Moderate.

*Juice*.—Moderate.

*Texture*.—Genetically melting, but remains firm and crisp throughout the harvest period.

*Fibers*.—Abundant, fine.

*Ripens*.—Fairly even.

*Flavor*.—Classic nectarine flavor, medium acidity, moderately sweet, typically 15 brix.

*Aroma*.—Moderate.

*Eating quality*.—Very good.

STONE

Type: Clingstone.

Form: Oval to elliptical.

Hilum: Narrow, oval.

Base: Rounded to somewhat truncate.

Apex: Acuminate.

Sides: Fairly equal.

Tip: Sharp, length 1/16" [1.6 mm.].

Surface: Irregularly furrowed toward the apex, pitted toward the base.

Ridges: Jagged.
External color: Moderate orange yellow [71. m.OY] when first removed.
Pit wall color when cracked: Deep yellowish brown [75. deep yBr].
Cavity surface color: Brownish orange [54. brO].
Average pit wall thickness: ¼" [6.4 mm.].
Average length: 1 9/16" [39.7 mm.].
Average width: 1 1/16" [27.0 mm.].
Average breadth: ¾" [19.1 mm.].
Tendency to split: None observed.
Kernel:
*Form*.—Oval.
*Skin color*.—Light orange yellow [70. l.OY].
*Pellicle color*.- Dark yellowish brown [78. d.yBr].
*Vein color*.—Strong orange yellow [68. s.OY].
*Taste*.—Bitter.
*Viable*.—Yes.
*Average length*.—⅞" [22.2 mm.].
*Average width*.—½" [12.7 mm.].
*Amygdalin*.—Abundant.

USE

Market: Fresh market and long distance shipping.
Keepinq quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'August Bright' (U.S. Plant Pat. No. 15,143) nectarine by being self-fertile, by having a now showy blossom, by blooming in the mid to late season, and by producing nectarines that mature in mid August and that are mostly red in skin color, yellow in flesh color, globose to slightly oblong in shape, clingstone in type, very good in flavor, but is distinguished therefrom by having a larger tree, by blooming more densely, by having globose instead of reniform leaf glands, and by producing fruit that is somewhat larger in size, that has much less skin freckling, that is sweeter in flavor, and that has a bitter instead of sweet kernel.

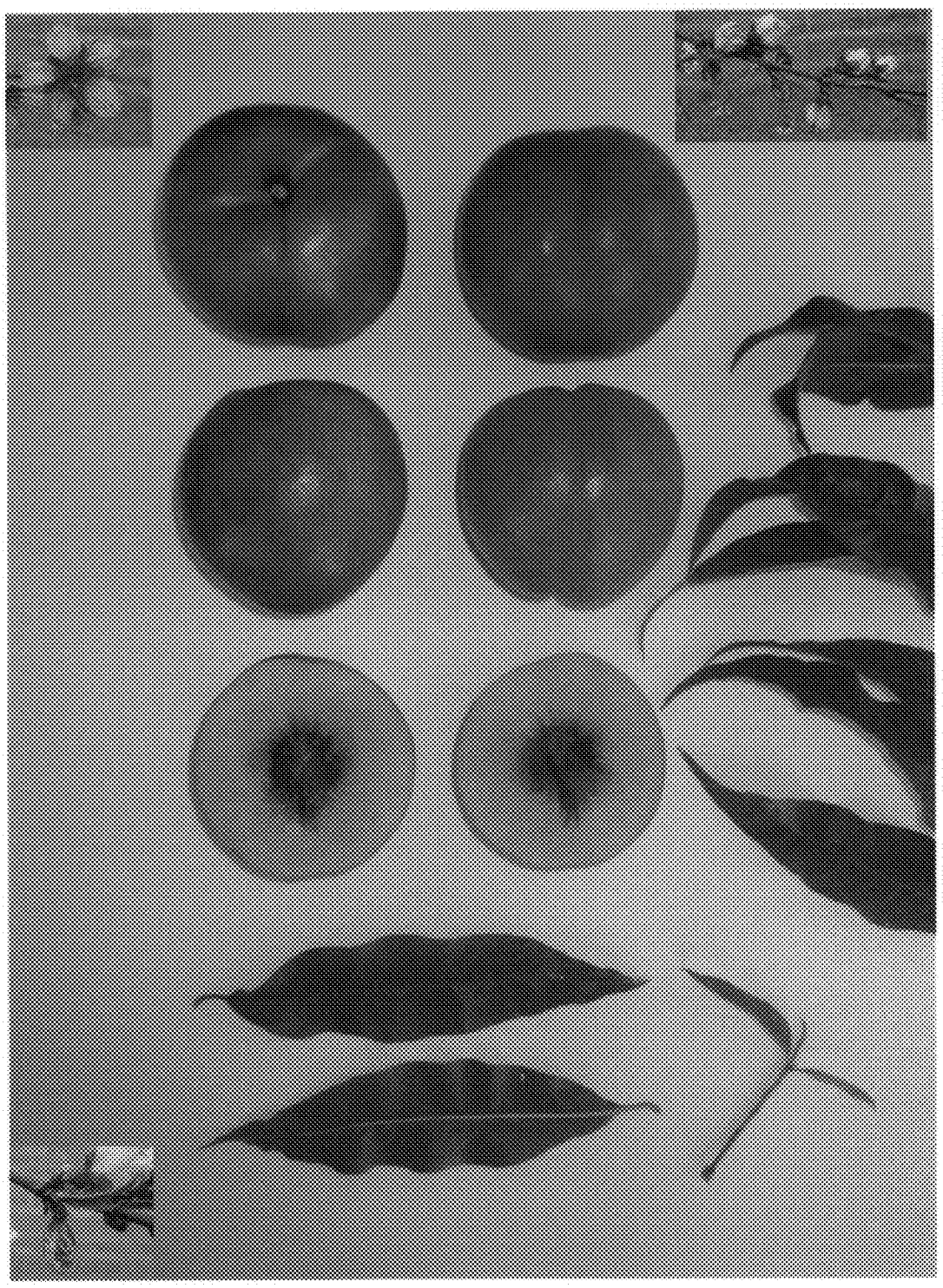

* * * * *